(12) United States Patent
Hu (10) Patent No.: US 11,338,097 B2
(45) Date of Patent: May 24, 2022

(54) ACTIVE SELF-LOCKING TYPE SYRINGE

(71) Applicant: Promisemed Hangzhou Meditech Co., Ltd., Hangzhou (CN)

(72) Inventor: Chaoyu Hu, Hangzhou (CN)

(73) Assignee: Promisemed Hangzhou Meditech Co., Ltd., Hangzhou (CN)

(*) Notice: Subject to any disclaimer, the term of this patent is extended or adjusted under 35 U.S.C. 154(b) by 14 days.

(21) Appl. No.: 16/954,454

(22) PCT Filed: Dec. 11, 2018

(86) PCT No.: PCT/CN2018/120170
§ 371 (c)(1),
(2) Date: Jun. 16, 2020

(87) PCT Pub. No.: WO2020/052122
PCT Pub. Date: Mar. 19, 2020

(65) Prior Publication Data
US 2021/0077745 A1    Mar. 18, 2021

(30) Foreign Application Priority Data

Sep. 12, 2018 (CN) .......................... 201811059998.7

(51) Int. Cl.
*A61M 5/32* (2006.01)
*A61M 5/31* (2006.01)
*A61M 5/315* (2006.01)

(52) U.S. Cl.
CPC .......... *A61M 5/326* (2013.01); *A61M 5/3129* (2013.01); *A61M 5/31501* (2013.01); *A61M 5/3202* (2013.01); *A61M 5/3293* (2013.01)

(58) Field of Classification Search
CPC .. A61M 5/326; A61M 5/3129; A61M 5/3202; A61M 5/3293; A61M 5/3271;
(Continued)

(56) References Cited

U.S. PATENT DOCUMENTS 9,480,799 B2 * 11/2016 Schraga ............... A61M 5/3234
10,220,156 B2 * 3/2019 Thornton ............... A61M 5/326
(Continued)

FOREIGN PATENT DOCUMENTS

CN 2678665 Y 2/2005
CN 101563124 A 10/2009
(Continued)

OTHER PUBLICATIONS

Kathleen Gold, Analysis: The Impact of Needle, Syringe, and Lancet Disposal, Jul. 2011, Diabetes Technology Society, vol. 5, pp. 848-850 (Year: 2011).*

*Primary Examiner* — Manuel A Mendez
(74) *Attorney, Agent, or Firm* — Muncy, Geissler, Olds & Lowe, P.C.

(57) ABSTRACT

An active self-locking type syringe includes a barrel, needle hub, plunger assembly, plunger protection cover, needle cap, needle tube, needle point protection sleeve, spring, guiding limit assemblies, initial clamping assemblies and a trigger ring plug. In an initial state, the trigger ring plug is located in a trigger cavity and is not in contact with the trigger parts or is in contact with the trigger parts but not enough to separate the initial clamping assemblies, the inner wall of the trigger ring plug and the needle hub are sealed, and the outer wall of the trigger ring plug and the inner wall of the barrel are sealed. In the above structure, the trigger ring plug arranged in the trigger cavity is triggered from the interior of the barrel close to a patient end, and the needle point protection sleeve is released.

13 Claims, 6 Drawing Sheets

(58) Field of Classification Search
CPC ............ A61M 2005/3261; A61M 5/32; A61M 5/2033; A61M 5/3213; A61M 5/50; A61M 5/20; A61M 5/322; A61M 5/3232; A61M 5/3234; A61M 5/3241
See application file for complete search history.

(56) References Cited

U.S. PATENT DOCUMENTS

2011/0288491 A1   11/2011  Newman et al.
2017/0143912 A1*   5/2017  Hu ........................ A61M 5/321

FOREIGN PATENT DOCUMENTS

| | | |
|---|---|---|
| CN | 102631729 A | 8/2012 |
| CN | 108430543 A | 8/2018 |

\* cited by examiner

ACTIVE SELF-LOCKING TYPE SYRINGE

TECHNICAL FIELD

The present invention relates to the field of safe syringes, and more particularly relates to an active self-locking type syringe.

BACKGROUND ART

Currently, there are lots of types of safe syringes on the market, which are generally grouped into two technical routes. One technical routes is a needle point retraction type safe syringe, that is, after injection is completed, a needle point can retract into a barrel or a needle point protection sleeve automatically or manually, and thus the risk that a user is stabbed by a used needle point is avoided. The other technical route is a trigger type safe syringe, that is, a needle point is fixed relative to a barrel, a needle point protection device capable of being triggered is usually arranged outside the barrel, in the injection process, the barrel axially moves relative to the needle point protection device, when injection is completed, the barrel or a plunger triggers the needle point protection device, and after being triggered, the needle point protection device can cover a needle tube to prevent needle point exposure.

The safe syringes based on the two above technical routes are relatively complex in structure and high in production cost, and therefore it is necessary to develop a novel safe syringe to overcome defects in the prior art.

SUMMARY OF THE INVENTION

A technical problem to be solved by the present invention is to provide a structure-improved active self-locking type syringe, and the active self-locking type syringe realizes triggering through an interior of a barrel, so that technical effects of simple structure, low cost and higher reliability are achieved.

To solve the above technical problem, a technical solution provided by the present invention is as follows. An active self-locking type syringe at least comprises:

a barrel, internally provided with a plunger assembly;

a needle hub, fixed at a position of an interior of the barrel close to a patient end, wherein a spring cavity close to one side of the patient end and a trigger cavity close to one side of the plunger assembly are formed between an outer wall of the needle hub and an inner wall of the barrel;

a needle tube, fixed on the needle hub and with a needle point stretching out from the patient end of the barrel;

a needle point protection sleeve, configured to cover the used needle tube;

a spring, located in the spring cavity and with an end close to the needle point being in contact with the needle point protection sleeve;

a guiding limit assembly, configured to limit a direction and an extreme position of axial movement of the needle point protection sleeve relative to the barrel after the needle point protection sleeve is triggered;

an initial clamping assembly, configured to keep the needle point protection sleeve in a non-triggered state and provided with a trigger part triggered from an interior of the trigger cavity to separate the initial clamping assembly; and a trigger ring plug, located in the trigger cavity and being not in contact with the trigger part or being in contact with the trigger part but not enough to separate the initial clamping assembly in an initial state, wherein an inner wall of the trigger ring plug and the needle hub are sealed, and an outer wall of the trigger ring plug and an inner wall of the barrel are sealed.

In a preferred embodiment, the active self-locking type syringe further comprises a non-return part configured to prevent the needle point protection sleeve from retracting in a protection state.

In a preferred embodiment, the non-return part comprises a non-return arm arranged at the patient end of the barrel, the non-return arm has elasticity, and a free end of the non-return arm protrudes from the outer wall of the barrel in a radial direction.

In a preferred embodiment, a slot hole is formed in a side wall of the needle point protection sleeve close to the patient end and runs through the side wall, and the slot hole is configured to accommodate the stretching non-return arm.

In a preferred embodiment, the plunger assembly comprises a plunger and a piston arranged at an end of the plunger, and the end of the plunger is a pushing part configured to push the trigger ring plug.

In a preferred embodiment, a matched embedding mechanism is arranged between an end of the needle hub away from the patient end and an end portion of an end of the plunger close to the needle hub.

In a preferred embodiment, the guiding limit assembly comprises a protruding column arranged on the outer wall of the barrel and a guiding limit groove formed in the side wall of the needle point protection sleeve, and the protruding column is matched with the guiding limit groove.

In a preferred embodiment, the initial clamping assembly comprises an elastic arm arranged on the needle point protection sleeve and a clamping groove running through the outer wall of the barrel, a clamping block extending into the needle point protection sleeve in a radial direction is arranged at a free end of the elastic arm, and the clamping block is clamped in a clamping ends of the clamping groove close to the patient end.

In a preferred embodiment, the trigger part comprises a trigger arm connected with a side of the clamping groove away from the clamping end, the trigger arm has elasticity, and in an initial state, a free end of the trigger arm is located on an inner side of the clamping block in a radial direction.

In a preferred embodiment, the free end of the elastic arm and the free end of the non-return arm abut against each other in a needle point protection state.

In a preferred embodiment, the free end of the elastic arm is lower than an end face of the needle point protection sleeve in an axial direction.

In a preferred embodiment, the active self-locking type syringe further comprises a needle cap sleeved over the needle point protection sleeve, and the needle cap covers the free end of the elastic arm in an initial state.

In a preferred embodiment, the active self-locking type syringe further comprises a plunger protection cover connected with an end of the barrel away from the patient end.

According to the active self-locking type syringe in the present embodiment, the trigger ring plug arranged in the trigger cavity is triggered from the interior of the barrel close to the patient end, and the needle point protection sleeve is released, so that technical purposes of needle point exposure prevention and self-locking are realized; and the trigger way is ingenious in design, no other part for assisting triggering exists except the barrel and the needle point protection sleeve, and the active self-locking type syringe has the technical advantages that the structure is simple, the radial dimension of the barrel is small, the components are concise, and the production cost is low.

DETAILED DESCRIPTION OF THE INVENTION

To make purposes, technical solutions and advantages of the present invention clearer, the present invention is further specifically illustrated with reference to drawings and embodiments in the following. It should be understood that specific embodiments described herein are only used for explaining the present invention rather than limiting the present invention.

Figure 1:
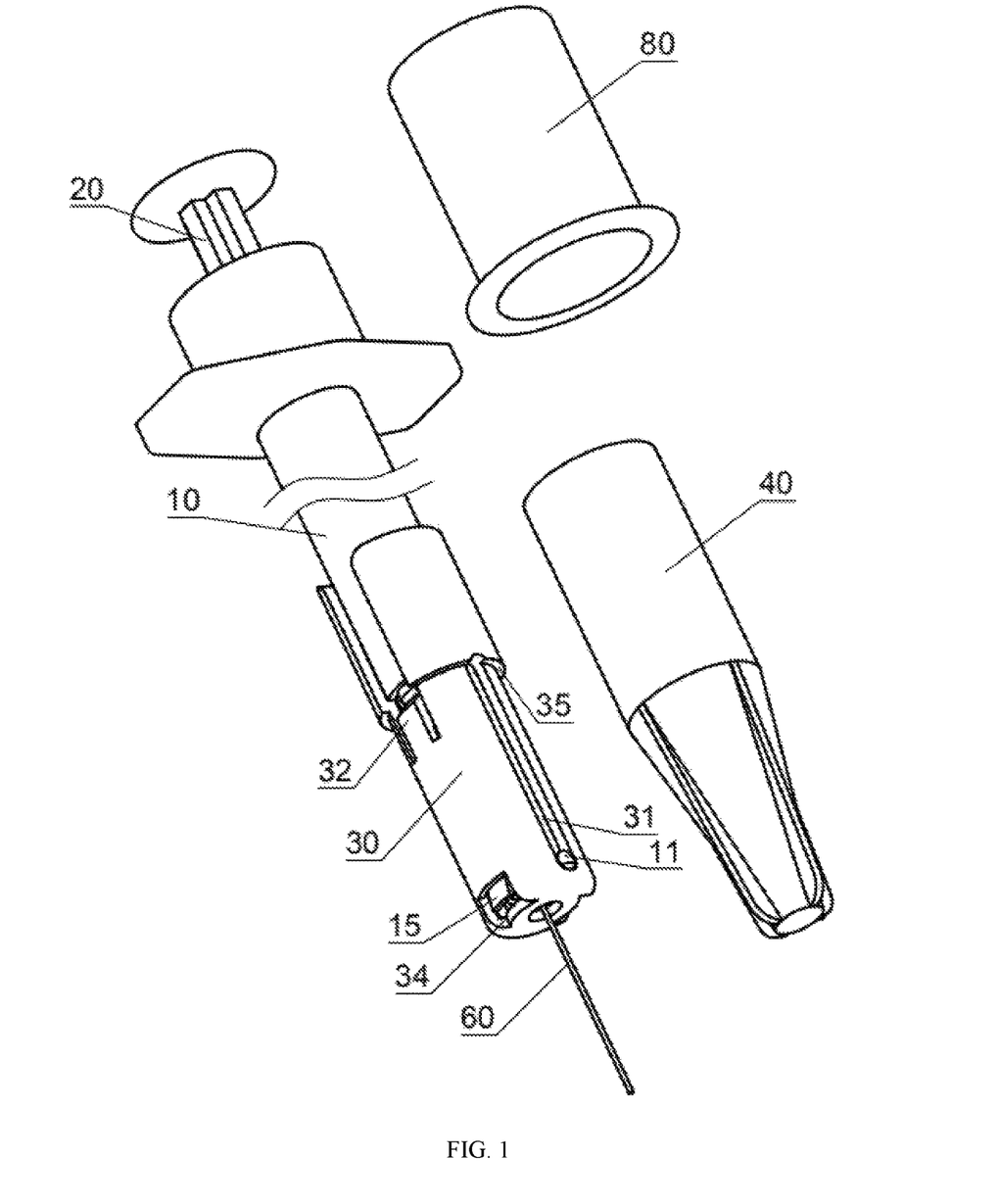
FIG. 1 is a schematic external structure diagram of an active self-locking type syringe according to the present embodiment.
Figure 2:
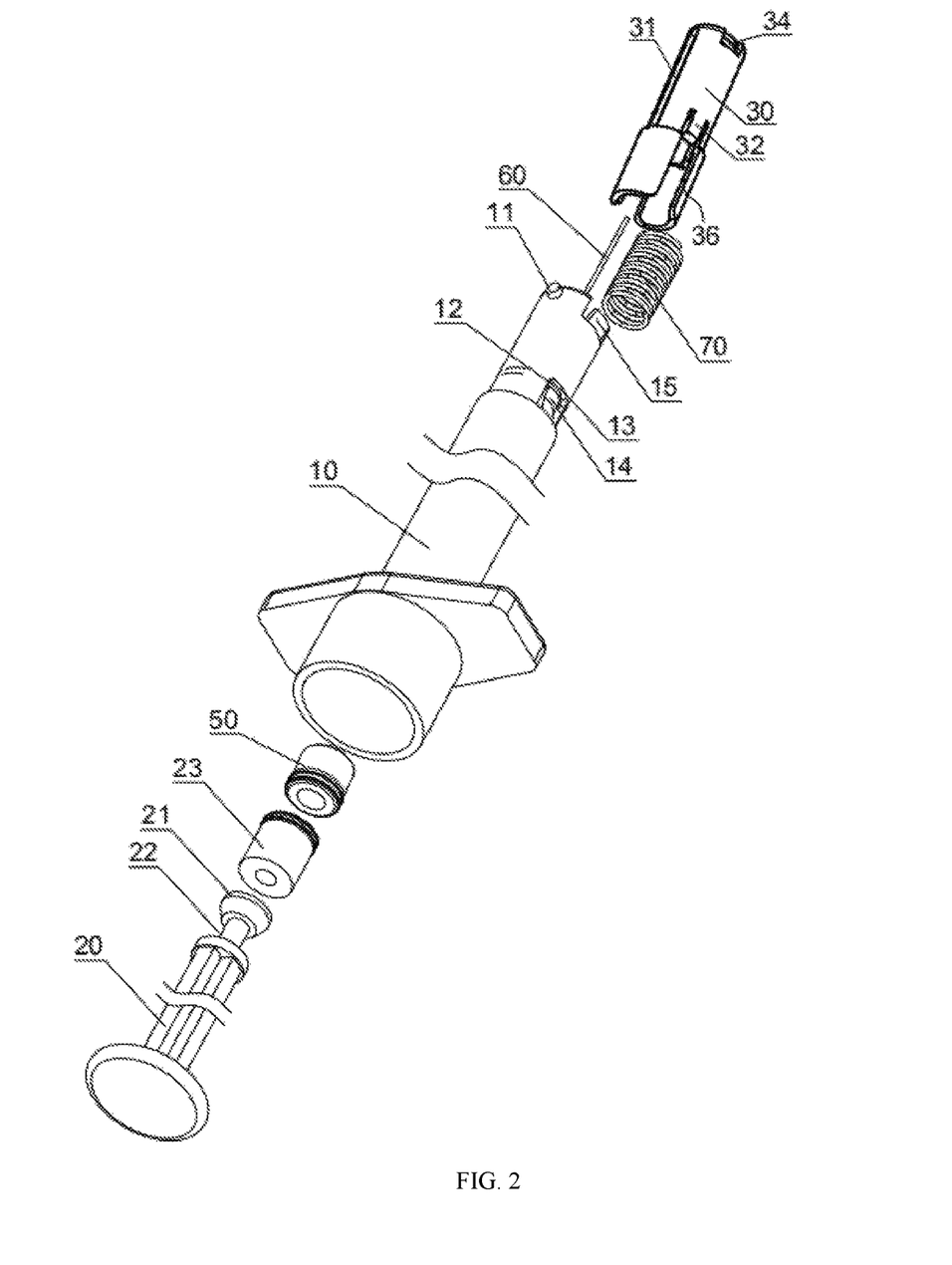
FIG. 2 is a schematic exploded structure diagram of the active self-locking type syringe according to the present embodiment.

As shown in FIG. 1 and FIG. 2, an active self-locking type syringe of the present embodiment includes a barrel 10, a plunger assembly, a needle tube 60, a needle point protection sleeve 30, a spring 70 and a needle cap 40. In the present embodiment, in order to illustrate the structure conveniently, the needle tube end of the active self-locking type syringe is defined as a patient end.

Figure 3:
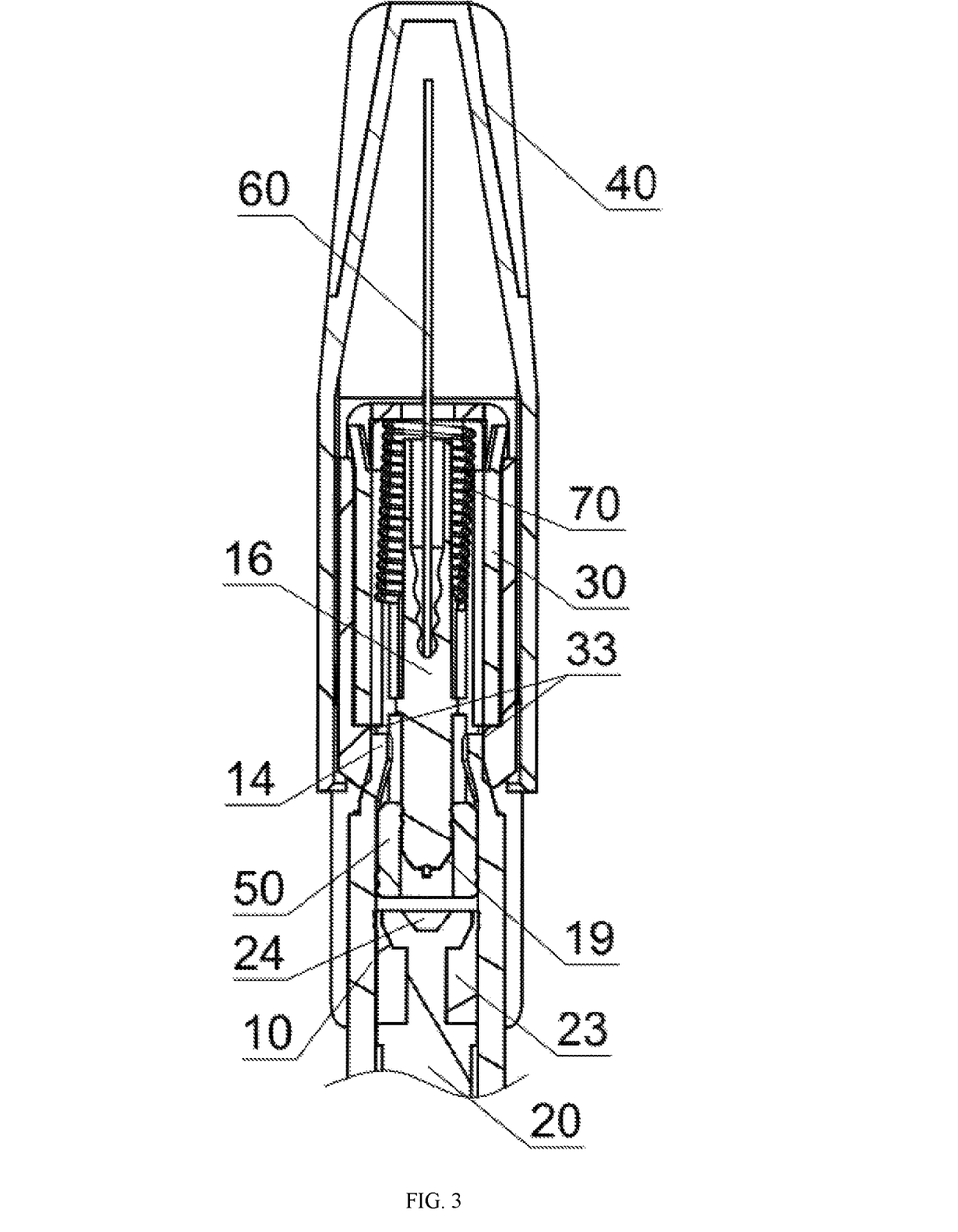
FIG. 3 is a local sectional view of the active self-locking type syringe (non-triggered) in an initial state according to the present embodiment.

In the present embodiment, the plunger assembly is assembled in the barrel, as shown in FIG. 2 and FIG. 3, the plunger assembly structurally comprises a plunger 20 and a plunger stopper 23, wherein a piston ring groove 22 is formed in the end of the plunger 20 close to the patient end, the plunger stopper 23 is sleeved with the piston ring groove 22, the plunger stopper 23 and the plunger 20 are a piston and a plunger commonly used in the prior art, the plunger stopper 23 is made of a flexible material, the plunger stopper 23 and the piston ring groove 22 are sealed, meanwhile, the plunger stopper 23 and the inner wall of the barrel 10 are sealed, and liquid medicine is sucked in and injected through pushing and pulling of the plunger assembly.

As modifications of the present embodiment, a pushing part 21 is arranged at one end of the plunger 20 and configured to push a trigger ring plug 50 to axially move, wherein the end face of the pushing part 21 is adaptive to the end face of the trigger ring plug 50.

Figure 4:
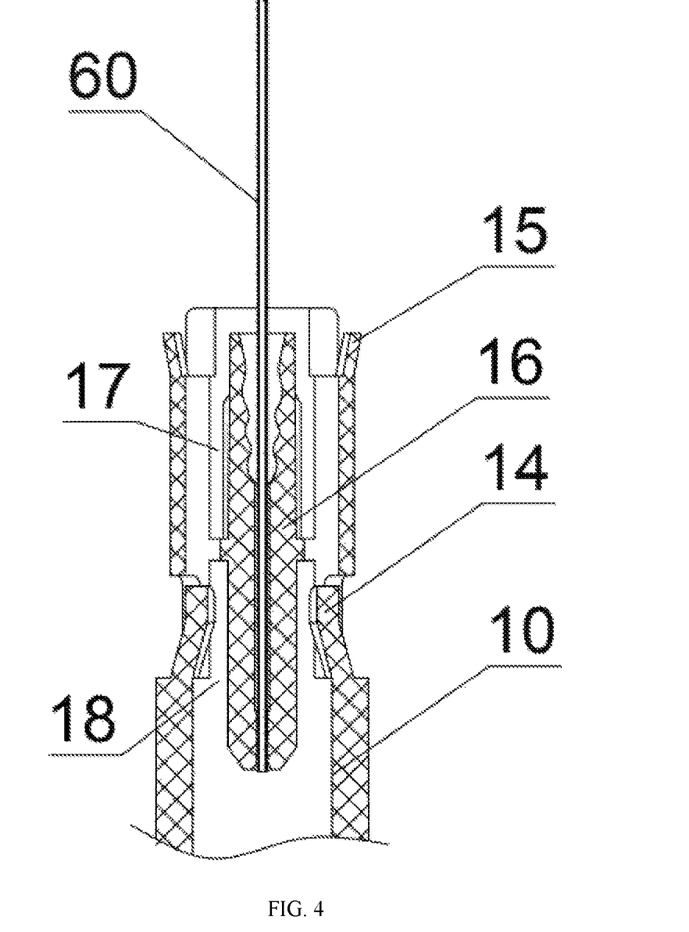
FIG. 4 is a local sectional view of a barrel of the active self-locking type syringe according to the present embodiment.

As modifications of the present embodiment, as shown in FIG. 4, a needle hub 16 is fixed at the position in the barrel 10 close to the patient end, the needle tube 60 is fixed to the needle hub 16, and a needle point stretches out from the patient end of the barrel 10. The outer wall of the needle hub 16 and the inner wall of the barrel are fixedly connected, and a spring cavity 17 close to the patient end side and a trigger cavity 18 close to the plunger assembly side are formed.

Figure 5:
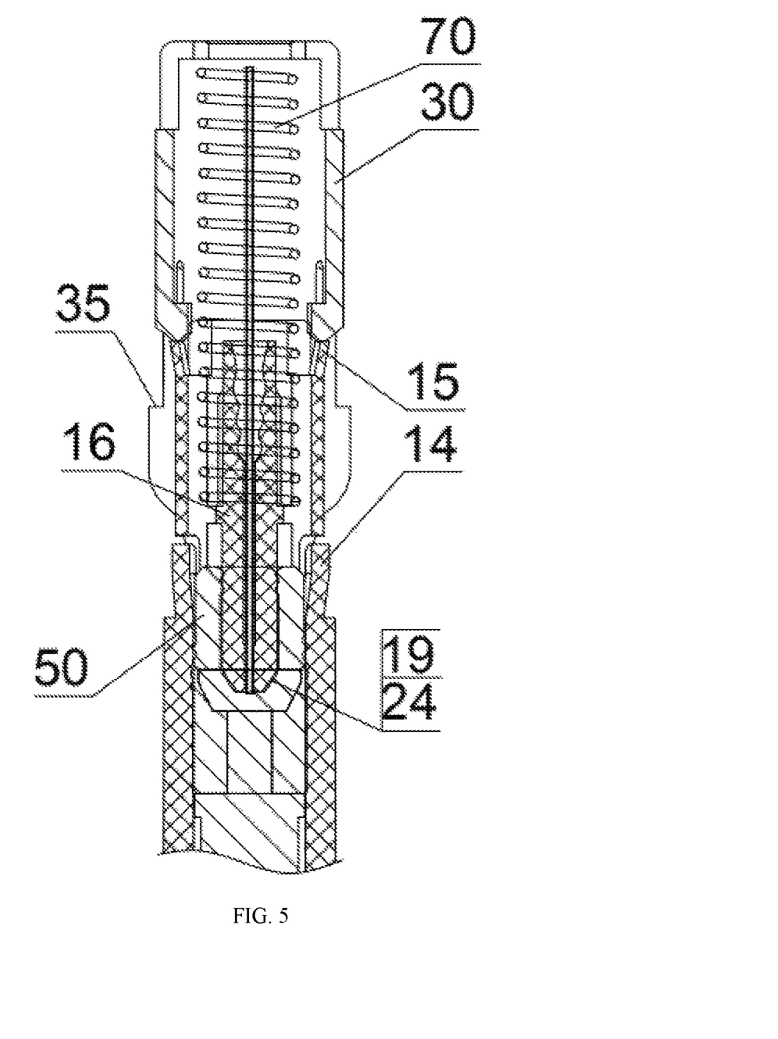
FIG. 5 is a local sectional view of the active self-locking type syringe in a needle point protection state according to the present embodiment.

In a preferred embodiment, as shown in FIG. 3 and FIG. 5, a matched embedding mechanism is arranged between the end of the needle hub 16 away from the patient end and the end portion of the end of the plunger 20 close to the needle hub, and configured to reduce the remaining amount of liquid medicine in the injection process. Preferably, the embedding mechanism comprises an outer conical surface 19 arranged at the end of the needle hub and a conical groove 24 formed in the end of the plunger. Certainly, the conical groove may also be formed in the end of the needle hub, and the outer conical surface is arranged at the end of the plunger. The outer conical surface and the conical groove may further be an outer arc surface and an arc groove. Same technological means in the art with technical conceptions being the same as the embedding mechanism of the present embodiment are all regarded as same technical solutions of the application.

As shown in FIG. 3 and FIG. 4, the trigger ring plug 50 is installed in the trigger cavity 18, the inner wall of the trigger ring plug 50 and the outer wall of the needle hub 16 are sealed, and the outer wall of the trigger ring plug 50 and the inner wall of the barrel are sealed. In the present embodiment, the trigger ring plug 50 may axially move in the trigger cavity, and the trigger ring plug 50 moves through pushing of the pushing part 21.

In the present embodiment, as shown in FIG. 3 and FIG. 4, the needle point protection sleeve 30 is configured to cover the used needle tube 60, and the needle point protection sleeve 30 is sleeved over the patient end of the barrel in an initial state. The spring 70 is arranged between the needle point protection sleeve 30 and the barrel and located in the spring cavity 17, and the end of the spring close to the needle point makes contact with the needle point protection sleeve. In an initial state, the spring 70 is in a compressed energy-storage state, and a pre-elastic force is provided for launching of the needle point protection sleeve.

In the present embodiment, initial clamping assemblies are arranged between the needle point protection sleeve 30 and the barrel 10, and configured to keep the needle point protection sleeve 30 in a non-triggered state. As shown in FIG. 2 and FIG. 3, each preferred initial clamping assembly of the present embodiment comprises an elastic arm 32 arranged on the needle point protection sleeve and a clamping groove 12 running through the outer wall of the barrel, clamping blocks 33 extending into the needle point protection sleeve in the radial direction is arranged at the free ends of the elastic arms 32, and the clamping blocks are clamped in clamping ends 13 of the clamping grooves close to the patient end.

It should be noted that the clamping grooves 12 are formed in the outer wall of the barrel where the trigger cavity 18 is located, the initial clamping assemblies further comprise trigger parts triggered from the interior of the trigger cavity 18 to separate the initial clamping assemblies. Preferably, the trigger parts comprise trigger arms 14 connected with the sides of the clamping grooves away from the clamping ends, the trigger arms 14 have elasticity, in an initial state, as shown in FIG. 3, the free ends of the trigger arms 14 are located on the inner sides of the clamping blocks in the radial direction.

In a preferred embodiment, as shown in FIG. 1 and FIG. 2, guiding limit assemblies are arranged between the needle point protection sleeve 30 and the barrel 10 and configured to limit the direction and the extreme position of axial movement of the needle point protection sleeve 30 relative to the barrel after the needle point protection sleeve 30 is triggered. Preferably, each guiding limit assembly in the present embodiment comprises a protruding column 11 arranged on the outer wall of the barrel and a guiding limit groove 31 formed in the side wall of the needle point protection sleeve, wherein the protruding column is matched with the guiding limit groove to limit relative rotation between the needle point protection sleeve 30 and the barrel 10 so that only axial movement may be made, and the end of the guiding limit groove 31 limits the extreme position of axial movement of the needle point protection sleeve 30.

In an initial state, the trigger ring plug 50 of the active self-locking type syringe of the present embodiment is located in the trigger cavity 18 and is not in contact with the trigger parts or is in contact with the trigger parts but not enough to separate the initial clamping assemblies. In the using process, the plunger assembly moves to the end away from the needle point firstly to suck liquid medicine into the barrel. In the injection process, the plunger assembly moves to the end of the needle point, in the pushing process of the plunger assembly, the pushing part 21 firstly makes contact with the trigger ring plug 50 and continues to push the trigger ring plug 50 to axially move after contact, the trigger ring plug 50 drives the trigger arms 14 to gradually expand outwards, the trigger arms 14 drive the clamping blocks 33 to gradually deform outwards in the radial direction, so the clamping blocks 33 and the clamping ends 13 are separated. The clamping blocks 33 and the clamping ends 13 are completely separated when the liquid medicine is injected, at the moment, since the needle tube has not been pulled out of the skin of a patient, the patient end of the needle point protection sleeve 30 is in contact with the skin of the patient, in the process that the needle tube is pulled out of the skin of the patient, potential energy stored by the spring 70 is released to drive the needle point protection sleeve 30 to cover the used needle tube, and therefore the needle tube is prevented from hurting people by exposure and self-locking is achieved.

As modifications of the present embodiment, the active self-locking type syringe further comprises non-return parts configured to prevent the needle point protection sleeve from retracting in a protection state. Preferably, as shown in FIGS. 2-5, the non-return parts of the present embodiment comprise non-return arms 15 arranged at the patient end of the barrel, the non-return arms 15 have elasticity, and the free ends of the non-return arms 15 protrude from the outer wall of the barrel in the radial direction.

As shown in FIG. 5, in a needle point protection state, the free ends of the elastic arms 32 and the free ends of the non-return arms 15 abut against each other to achieve self-locking. Due to the fact that the non-return arms 15 protrude from the outer wall of the barrel in the radial direction and the outer diameter of the free ends of the non-return arms 15 is greater than the outer diameter of the free ends of the elastic arms 32, the needle point protection sleeve may be prevented from retracting, and the protection reliability is good through the non-return parts.

In a preferred embodiment, as shown in FIGS. 1-3, slot holes 34 are formed in the side wall of the needle point protection sleeve 30 close to the patient end and run through the side wall, and the slot holes 34 are configured to accommodate the stretching non-return arms in the initial state.

In a preferred embodiment, as shown in FIG. 2, a through groove 36 is formed in the outer wall of the needle point protection sleeve, and the elastic arms 32 are located in the through groove 36. The free ends of the elastic arms 32 may be higher or lower than the end face of the needle point protection sleeve 30 in the axial direction, and may also be flush with the end face of the needle point protection sleeve 30. Preferably, the free ends of the elastic arms 32 are lower than the end face of the needle point protection sleeve 30 in the axial direction. Such arrangement is to reduce the stroke of the needle point protection sleeve to guarantee that the launching force of the spring may launch the needle point protection sleeve in place.

Figure 6:
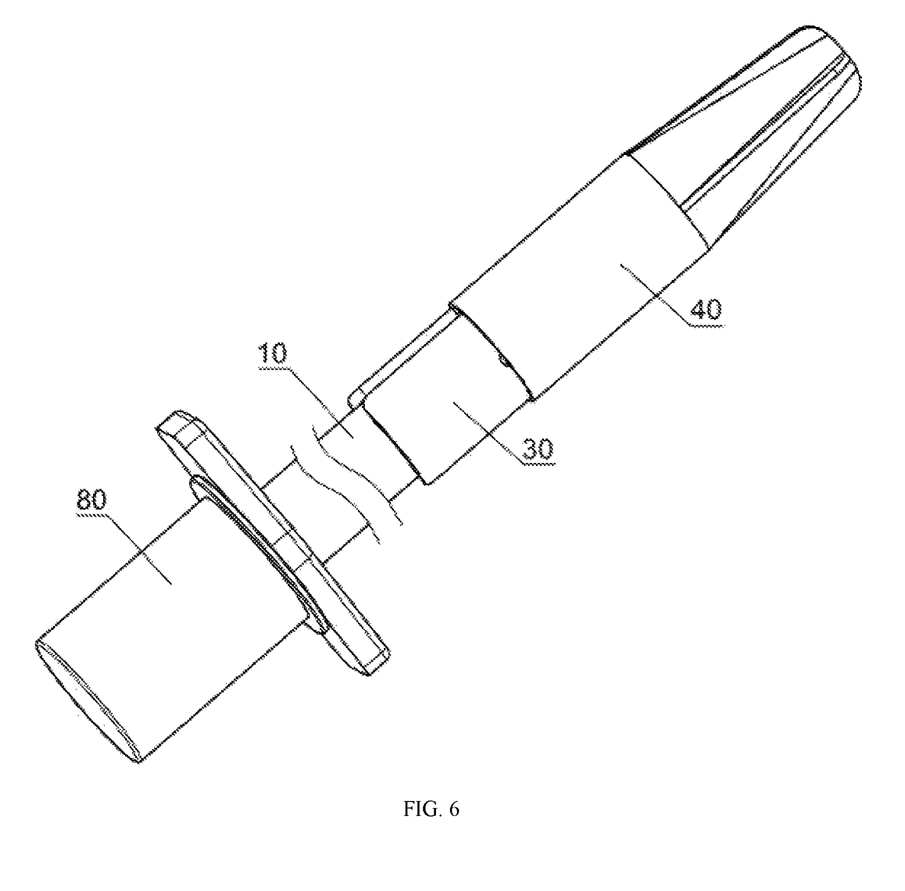
FIG. 6 is a schematic structure diagram of the active self-locking type syringe in an unused state according to the present embodiment.

In a preferred embodiment, as shown in FIG. 1 and FIG. 6, the active self-locking type syringe of the present embodiment further comprises a plunger protection cover 80, and the plunger protection cover 80 is sleeved over the end of the barrel away from the patient end in an initial unused state and configured to prevent pushing of the plunger so as to avoid mistaken triggering of the needle point protection sleeve.

In a preferred embodiment, as shown in FIG. 1 and FIG. 6, the needle cap 40 is sleeved over the needle point protection sleeve 30, and preferably, the needle point protection sleeve is further provided with a stepped surface 35 connected with the end of the needle cap. It should be noted that when the needle cap is installed on the needle point protection sleeve, the needle cap covers the free ends of the elastic arms 32. Such arrangement is to achieve the purpose that even though the plunger is pushed, the trigger ring plug cannot enter trigger space in the trigger arms due to the fact that the elastic arms 32 are pressed and do not have deformation space, and mistaken triggering of the needle point protection sleeve can still be avoided.

It should be noted that in the present embodiment, there are two groups of guiding limit assemblies, two groups of initial clamping assemblies and two groups of non-return parts, and the components are evenly distributed in the circumferential direction. Certainly, this is the most exemplary embodiment, the guiding limit assemblies, the initial clamping assemblies and the non-return parts can further be arranged to be one group or three or more groups, and three or more groups of guiding limit assemblies, three or more groups of initial clamping assemblies and three or more groups of non-return parts are distributed in the circumferential direction and preferably are evenly distributed in the circumferential direction.

In a word, the above mentioned is only exemplary embodiments of the invention and not configured to limit the present invention, and any change, equal replacements and modifications made within the spirit and principle of the present invention should fall in the scope of protection of the present invention.

The invention claimed is:
1. An active self-locking type syringe, comprising at least:
a barrel, internally provided with a plunger assembly;
a needle hub, fixed at a position of an interior of the barrel close to a patient end, wherein a spring cavity close to one side of the patient end and a trigger cavity close to one side of the plunger assembly are formed between an outer wall of the needle hub and an inner wall of the barrel;
a needle tube, fixed on the needle hub and with a needle point stretching out from the patient end of the barrel;
a needle point protection sleeve, configured to cover the used needle tube;
a spring, located in the spring cavity and with an end close to the needle point being in contact with the needle point protection sleeve;
a guiding limit assembly, configured to limit a direction and an extreme position of axial movement of the needle point protection sleeve relative to the barrel after the needle point protection sleeve is triggered;
an initial clamping assembly, configured to keep the needle point protection sleeve in a non-triggered state and provided with a trigger part triggered from an interior of the trigger cavity to separate the initial clamping assembly; and a trigger ring plug, located in the trigger cavity, being not in contact with the trigger part or being in contact with the trigger part but not enough to separate the initial clamping assemblies in an initial state, with an inner wall being sealed with the needle hub, and with an outer wall being sealed with an inner wall of the barrel.

2. The active self-locking type syringe according to claim 1, further comprising a non-return part configured to prevent the needle point protection sleeve from retracting in a protection state.

3. The active self-locking type syringe according to claim 2, wherein the non-return part comprises a non-return arm arranged at the patient end of the barrel, the non-return arm has elasticity, and a free end of the non-return arm protrudes from the outer wall of the barrel in a radial direction.

4. The active self-locking type syringe according to claim 3, wherein a slot hole is formed in a side wall of the needle point protection sleeve close to the patient end and runs through the side wall, and the slot hole is configured to accommodate the stretching non-return arm.

5. The active self-locking type syringe according to claim 2, wherein the initial clamping assembly comprises an elastic arm arranged on the needle point protection sleeve and a clamping groove running through the outer wall of the barrel, a clamping block extending into the needle point protection sleeve in a radial direction is arranged at a free end of the elastic arm, and the clamping block is clamped in a clamping end of the clamping groove close to the patient end.

6. The active self-locking type syringe according to claim 5, wherein the trigger part comprises a trigger arm connected with a side of the clamping groove away from the clamping end, the trigger arm has elasticity, and in an initial state, a free end of the trigger arm is located on an inner side of the clamping block in a radial direction.

7. The active self-locking type syringe according to claim 6, further comprising a needle cap sleeved over the needle point protection sleeve, and the needle cap covers the free end of the elastic arm in an initial state.

8. The active self-locking type syringe according to claim 5, wherein the free end of the elastic arm and the free end of the non-return arm abut against each other in a needle point protection state.

9. The active self-locking type syringe according to claim 8, further comprising a needle cap sleeved over the needle point protection sleeve, and the needle cap covers the free end of the elastic arm in an initial state.

10. The active self-locking type syringe according to claim 1, wherein the plunger assembly comprises a plunger and a plunger stopper arranged at an end of the plunger, and the end of the plunger is a pushing part configured to push the trigger ring plug.

11. The active self-locking type syringe according to claim 10, wherein a matched embedding mechanism is arranged between an end of the needle hub away from the patient end and an end portion of an end of the plunger close to the needle hub.

12. The active self-locking type syringe according to claim 1, wherein the guiding limit assembly comprises a protruding column arranged on the outer wall of the barrel and a guiding limit groove formed in the side wall of the needle point protection sleeve, and the protruding column is matched with the guiding limit groove.

13. The active self-locking type syringe according to claim 1, further comprising a plunger protection cover connected with an end of the barrel away from the patient end.

* * * * *